US006845879B2

(12) United States Patent
Park

(10) Patent No.: US 6,845,879 B2
(45) Date of Patent: Jan. 25, 2005

(54) VENDING MACHINE FOR ORIENTAL TEA AND METHOD FOR VENDING THE TEA

(76) Inventor: Dong-Ok Park, 1020-601, Samsung APT., #101, Emae-dong, Bundang-gu, Seongnam-si, Gyeonggi-do (KR)

( * ) Notice: Subject to any disclaimer, the term of this patent is extended or adjusted under 35 U.S.C. 154(b) by 27 days.

(21) Appl. No.: 10/344,811
(22) PCT Filed: Sep. 24, 2001
(86) PCT No.: PCT/KR01/01592
§ 371 (c)(1), (2), (4) Date: Feb. 14, 2003
(87) PCT Pub. No.: WO02/25608
PCT Pub. Date: Mar. 28, 2002

(65) Prior Publication Data
US 2003/0173370 A1 Sep. 18, 2003

(30) Foreign Application Priority Data
Sep. 25, 2000 (KR) ........................................ 2000/56313

(51) Int. Cl.$^7$ .............................................. G07F 11/00
(52) U.S. Cl. ........................................ 221/13; 221/92
(58) Field of Search .............................. 221/2, 3, 7, 9, 221/13, 15, 92, 94, 123, 124

(56) References Cited

FOREIGN PATENT DOCUMENTS

| JP | 05-108937 | 4/1993 | ............. G07F/9/02 |
| JP | 09-330462 | 12/1997 | ............. G07F/9/02 |
| JP | 10-269431 | 10/1998 | ........... G07F/11/00 |
| KR | 1020000049946 | 8/2000 | ........... G07F/17/00 |

OTHER PUBLICATIONS

Korean Patent Abstract, 1020000049946; Aug. 5, 2000.*
English Abstract of JP 05–108937.
English Abstract of JP 09–330462.
English Abstract of JP 10–269431.
English Abstract of KR 1020000049946.

* cited by examiner

Primary Examiner—Kenneth Noland
(74) Attorney, Agent, or Firm—Cantor Colburn LLP

(57) ABSTRACT

The present invention provides a vending machine for oriental tea and method for vending the tea. The vending machine comprises a monitor, a monetary detection part, a pulse detection part detecting the user's pulse, an iris photograph part for photographing the user's iris, an oriental tea selection switch, a data input part, a controller for deciding the health condition of the user, a plurality of oriental medicine material storage barrel, discharge controlling part, and a mix and heat part for mixing and heating a certain water and various oriental medicine tea.

5 Claims, 4 Drawing Sheets

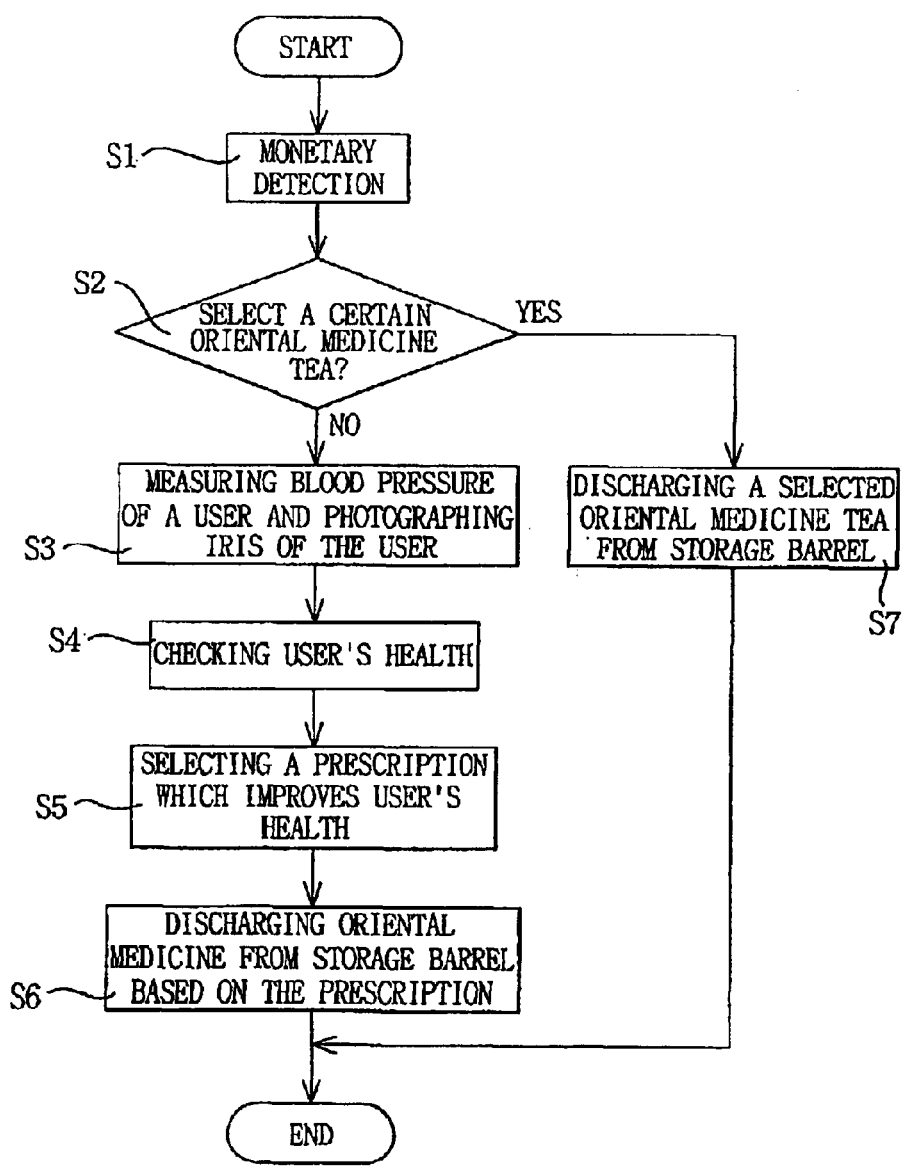

VENDING MACHINE FOR ORIENTAL TEA AND METHOD FOR VENDING THE TEA

TECHNICAL FIELD

The present invention relates to a vending machine for oriental tea and method for vending the tea, more particularly to a oriental or Chinese medicine tea vending machine which check user's health condition automatically and can provide the oriental tea by mixing various oriental medicine powder appropriately in accordance with user's health condition (disease).

BACKGROUND ART

Generally, vending machines which sell a product selected by a user among many kinds of products comprise, for example such as coffee vending machine which discharge a cup filled with selected coffee, sugar and water when the user puts coins in the vending machine that keeps various coffee, sugar and water in each storage barrel.

If the oriental tea or Chinese medicine tea are sold by mixing various highly concentrated oriental medicine material power appropriately by using a principle of the said coffee vending machine and an iris diagnosis method which is utilized in diagnosis of human health, it not only contribute to the nation's health also can obtain foreign currency by exporting equipment and medicinal herbs.

The iris diagnosis method is to diagnose human disease by detecting a shape and location of an autonomic nerve surrounding pupil of human and it is already utilized at many herb clinic or hospitals for internal diseases.

A pupil is located in the middle of the iris (the pupil of the eye). The pupil changes its size depend upon light's luminosity. A membrane like a fence is form round between a pupil and a pupil of the eye ⅓ ahead of outside of pupil edge. A line, which is surrounding pupil, is an autonomic nerve. The autonomic nerve is the center of the organization of the human body and the shape of autonomic nerve line reveals a condition of digestive organ. The autonomic nerve is spread the internal organs, blood vessels, etc., and, it controls each function necessary to life maintenance unconsciously, automatically and reflectively. For instance, the heart always keeps beating regularly while sleeping. The autonomic nerve is comprised of the sympathetic nerve and the parasympathetic nerve and is disposed in same organ. The functions of the two nerves are substantially opposite each other.

The sympathetic nerve and parasympathetic nerve are spread in various organs of same internal organ and govern the function against each other. For example, as for sympathetic nerve, it makes the pulsation of the heart intense but the parasympathetic nerve makes the pulsation of the heart slow. Namely, the two nerves cooperate each other by opposite function and the function of each organ is controlled as a result. The nerves are governed autonomously by the medulla oblongata or the backbone in diencephalon. Furthermore, the sympathetic nerve is related with adrenaline but the parasympathetic nerve is related with acetylcholine. The portion, which the autonomic nerve governs, is excessively important organ in life maintenance. Especially, the autonomic nerve governs the stomach and the intestines of the digestive system among internal organs regardless of their intention and the digestion motion is suppressed in function of the sympathetic nerve and is promoted in function of the parasympathetic nerve. The function of the kidney, a center of blood circulation, is strengthened by the parasympathetic nerve and is suppressed by the parasympathetic nerve. The breath can be controlled up to a certain point but it is usually governed by autonomic nerve. Thus, the organs of the body are controlled by the function of a nervous system.

The present applicant would like to emphasis repeatedly that a shape of iris membrane which shows autonomic nervous system shows the condition of digestive organs. Inside of the autonomic nervous line indicates stomach and intestines, the large intestine is connected with almost all of viscera and the large intestine has possibility to have an effect on viscera correspond to it. 85% of all diseases are nearly caused because of the large intestine. The autonomic nervous membrane of healthy man forms an almost circle and is located in ⅓ far from the pupil.

It is the iris diagnosis method that can know health condition by using shape of the autonomic nervous membrane and the distance from the pupil. For instance, when the autonomic nerve line droops, the large intestine become to droop so the large intestine especially press down the uterus and the bladder in the case of woman so that it disrupts the normal activity and it causes various pains such like menstrual colic or cystitis but if the said autonomic nerve line is saved as data and data about diseases and a prescription hereupon is constructed in memory territory of a controller which controls the operation of the vending machine, it provides the best oriental medicine tea to the user.

DISCLOSURE OF INVENTION

Therefore, the object of the present invention is to provide a vending machine for oriental tea and method for vending the tea which check user's health condition automatically and further can provide oriental medicine tea by mixing various oriental medicine powder appropriately according to the user's health condition (disease).

To achieve such object, the oriental medicine tea vending machine according to the present invention comprises: a monitor for displaying manual of the vending machine, a user's pulse and health condition and advertising screen; a monetary detection part for detecting whether coins (bills) or credit card are inputted or not to operate the vending machine; a pulse detection part detecting the user's pulse and outputting data corresponding to the pulse; an iris photograph part for photographing the user's iris and outputting data corresponding to the iris; an oriental tea selection switch for selecting any one of a kind of oriental medicine tea; a data input part for inputting data corresponding to sex, age, weight of the user; a controller for deciding the health condition of the user based on data signals outputted from the blood pressure detection part, the iris imaging part, the data input part and the oriental medicine selection switch and simultaneously outputting control signals which select various oriental medicine materials and contents which improves the health condition of the user; a plurality of oriental medicine material storage barrel which store various oriental medicine materials; a discharge controlling part which is installed around discharge hole of each of the oriental medicine material storage barrel and controls discharge quantity of various oriental medicine tea discharged from each oriental medicine storage barrel according to control signals outputted from the controller; and a mix and heat part for mixing and heating a certain water and various oriental medicine tea discharged from the oriental medicine storage barrel and providing the oriental tea in a cup.

BRIEF DESCRIPTION OF DRAWINGS

FIG. 3 is a flowchart showing operation of the vending machine according to the present invention.

BEST MODE FOR CARRYING OUT THE INVENTION

A preferred embodiment according to present invention is explained in conjunction with drawings by way of example.

Figure 1:
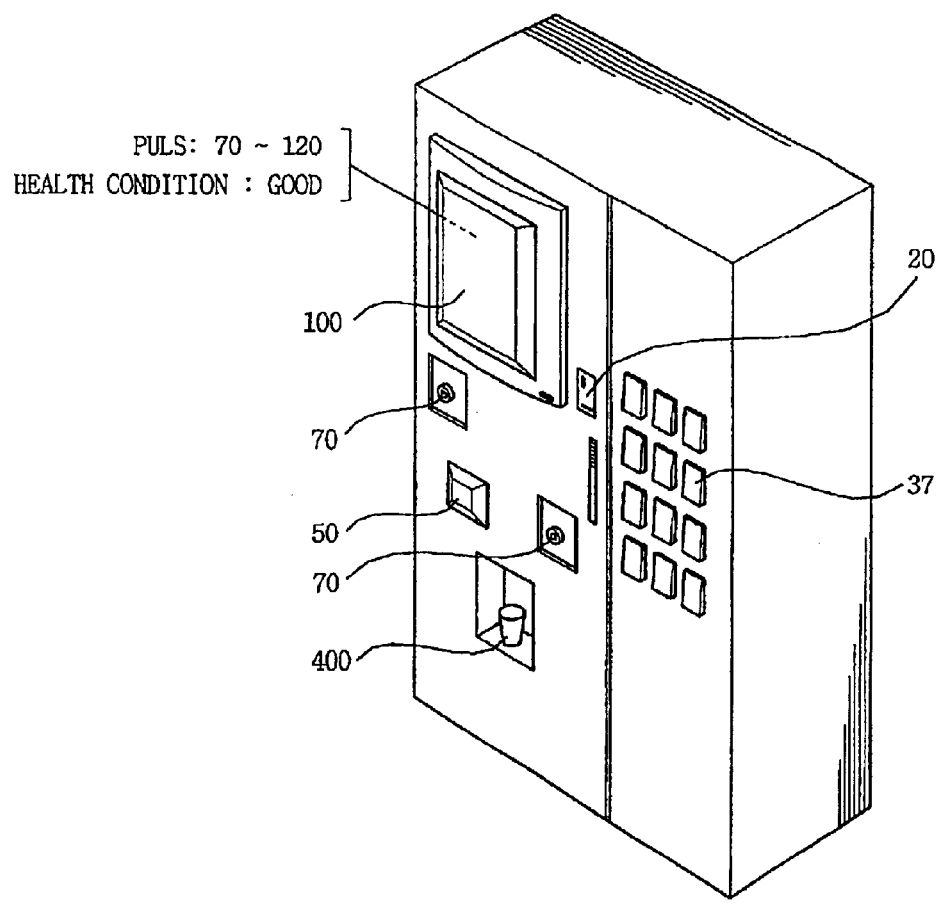
FIG. 1 is a perspective view showing one embodiment of a oriental medicine tea vending machine according to the present invention.
Figure 2A:
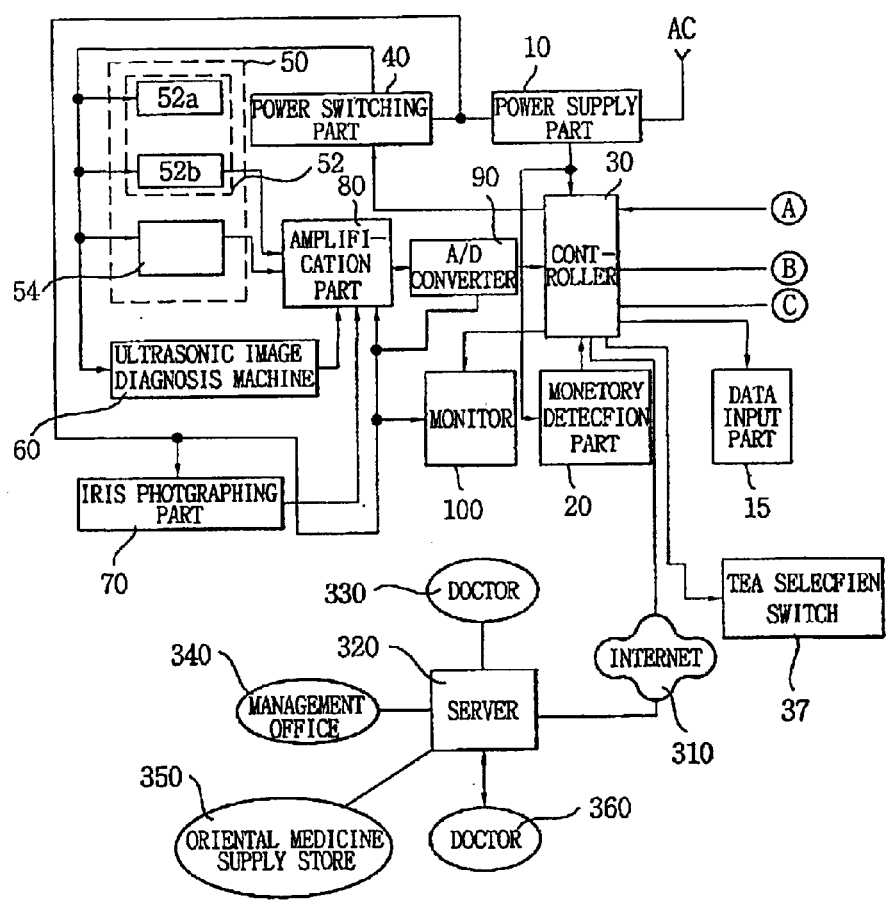
FIGS. 2a and 2b are block diagram showing circuits settled inside of the present invention.
Figure 2B:
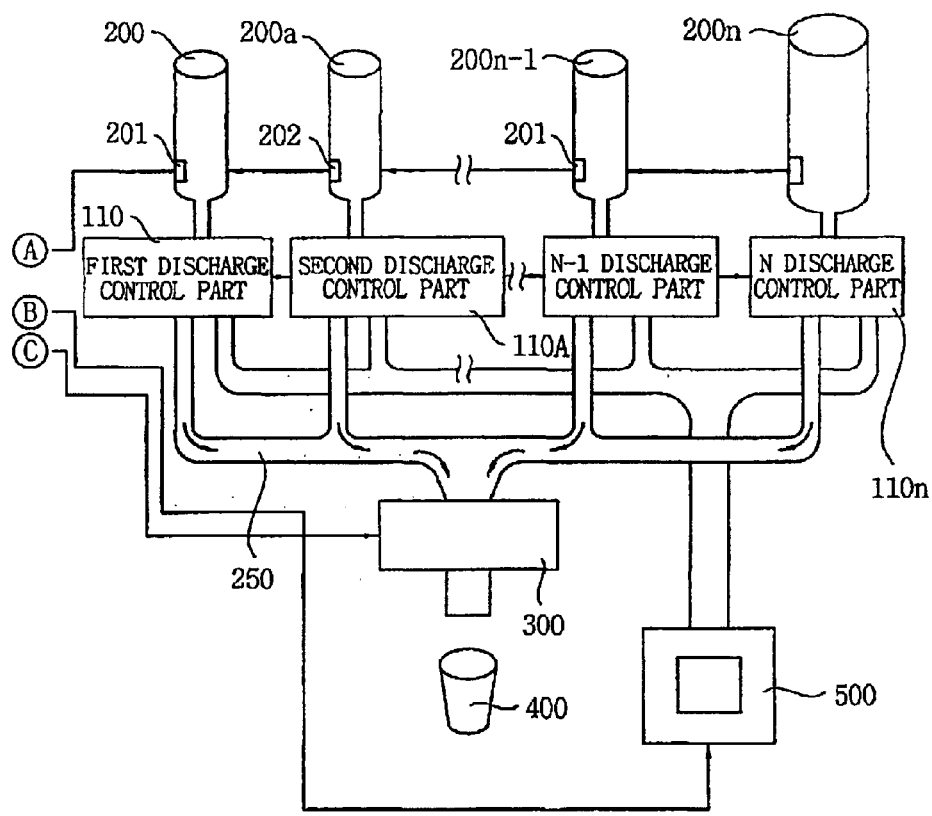

As shown in FIGS. 1 and 2, a power switching part 40 is composed to supply electric power to a blood pressure detection part 50 and an iris photographing part 70 by switching drive power generating from a power supply part 10 according to a power switching control signal generating from a controller 30 when money is detected in a monetary detection part 20, a monitor 100 is installed on the top front of the vending machine to display a manual of the vending machine and the pulse and a health condition of user.

The monetary detection part 20 is composed to detect coins (bills) or credit card for utilizing the vending machine and to supply data hereupon to a controller 30, and a data input part 15 is composed to input data corresponding to sex, age and weight of the user.

The pulse detection part 50 as a means for diagnosing the user's health condition is consisted of a pulse detection part 52 and an electrocardiogram wave sensor 54 formed outside the vending machine, wherein the pulse detection part 52 is consisted of a light emitting diode 52a for measuring a blood stream and a phototransistor 52b as light receiving element and the electrocardiogram wave sensor 54 is consisted of an electrode for detecting electrocardiogram wave, and an ultrasonic image diagnosis machine 60 is composed to output data which corresponds to a specific portion of the user photographed with ultrasonic waves.

Also, the iris photographing part 70 is consisted of infrared rays camera or general CCD camera for photographing iris of the user and outputting data corresponding to the photographed iris image, and an analog/digital converter 90 is composed to supply the signal to the controller 30 by changing it as a digital signal when the signals outputted from the blood pressure detection part 50, the ultrasonic image diagnosis machine 60 and the iris photographing part 70 inputted through an amplification part 80.

The controller 30 decides the user's health condition depend upon data outputted from the blood pressure detection part 50, the iris photographing part 70 and ultrasonic image diagnosis machine 60, the controller 30 is provided with a program in order to output control signals which choose various oriental materials and contents which improve the user's health condition, the 1 or the n discharge amount control part 110–110n is set up around the discharge hole of high concentrated oriental medicine powder storage barrels 200, 200a, - - - , 200n which store various oriental medicine powders and is composed of a stepped motor and a screw which is combined to a shaft of the stepped motor in order to control discharge content of oriental medicine in a state of powder automatically which is in oriental medicine powder storage barrel depend upon control signal outputted from the controller 30.

Further, inside of a low side of the high concentrated oriental medicine powder storage barrels 200, 200a, - - - , 200n are equipped a sensor as a remnants detection part 201, 202, when the amount of the high concentrated oriental medicine powder is less than a regular amount the sensor detects it and supply a data corresponding to the amount to the monitor through the controller 30 so that the monitor can display the remnants or supply to a sever 320 through internet 310 so that a management office 340 and oriental medicine material supply store 350 can know the fact and the signal from the iris photographing part 70 or the ultrasonic image diagnosis machine 60 is supplied to a doctor terminal 360 or a herb doctor terminal 330 through the internet 310 and the sever 320 so that the doctors can diagnosis user's health condition.

A mixing and heating part 300 is composed to mix and heat various oriental medicine material discharged from the oriental medicine storage barrel 200 and regular water discharged from the water tank 200n and to drop the oriental medicine tea into cup, and the oriental medicine discharged from the 1–n discharge quantity control parts 110, 110n can be packaged in a powder packing part 500 if the user wishes.

The operation of the oriental medicine tea vending machine as above said is as following.

For example, the oriental medicine tea vending machine according to the present invention is installed in public baths, a waiting room or premises of subway station as displaying manual in the monitor 100.

If a user inserts regular coins or bills to the monetary detection part 20 of the oriental medicine tea vending machine installed in the places, the controller 30 detects it and supplies switching control signal to the power switching part 40 and supplies electric power to the blood pressure detection part 50, a ultrasonic image diagnosis machine 60 and the iris photographing part 70, and explains manual again through speaker or monitor which is omitted in the drawing.

In such situation, the user presses the light emitting diode 52a for blood stream measurement that is the constituent element of the pulse sensor 52 and the photo transistor 52b using a finger of one hand and simultaneously presses electrode for electrocardiogram wave detection that is the constituent element of electrocardiogram wave sensor 54 using a finger of other hand.

At this time, in the process that the light of infrared rays range projected from the light emitting diode 52a for measuring blood stream goes into as incidence upon a photo transistor 52b as light receiving elements reflected afterward getting through the surface of the skin, the hemoglobin in the blood absorb light of specific wave length. Namely, the quantity of incidence light can be measured by the absorption function which is caused by signal of hemoglobin in the blood, there is a difference in the quantity of incidence light because the number of hemoglobin differs depend on the streaming blood. Accordingly, the quantity of blood stream that pass through the tip of a finger depend on pulse change periodically, and the changed value is transmitted to the photo transistor 52b so that it shows the voltage difference based on the value.

Moreover, the method for detecting an electrocardiogram wave detection is to detect R wave generating when the heart is pumping, wherein the R wave is transferred to the surface of a finger on the electrode for detecting electrocardiogram wave at the same time the heart beats and the wave is detected though the electrode for detecting electrocardiogram wave detection of as electrocardiogram wave sensor 54.

That is, what occurring in the heart's beating measures in two ways at the same time, wherein the difference of two signals means that detection times are different each other. In a case of pulse detection through blood stream quantity, it takes a certain time to reach a finger from the heart by various reasons such as a shape of blood pipe, etc., while in a case of an electrocardiogram wave, it can be detected as the nearly same time of the heart shrinkage.

The data outputted from the pulse sensor 52 and the electrocardiogram wave sensor 54 of the said blood pressure detection part 50 are amplified more than a certain level by the amplification part 80 and then is converted to a digital data through analog/digital converter 90 to be supplied to the controller 30, wherein the controller 30 utilizes the data to check user's health to measure the highest and lowest blood pressure level of the user.

Further, the controller 30 checks the health condition of a user by using data of blood pressure and iris pattern of the user when the controller 30 receives data photographed in the ultrasonic image diagnosis machine 60 and the iris photographing part 70 and age, sex, weight and a mike (not shown) of the user inputted in a data input part 15. For instance, the controller 30 supplies a discharge quantity control signal to the 1 or the n discharge quantity control part optionally installed around a discharge hole of a high concentrated oriental medicine storage barrels 200, 200a, - - - , 200n which store various oriental medicine powder, if the user has a headache, a oriental medicine tea based on oriental medicine powder which can reduce the headache is served to the user, if the user has an articulation inflammation, a oriental medicine tea based on oriental medicine powder which can reduce the articulation inflammation is served to the user, or if the user has a menstruation pain, a oriental medicine tea based on oriental medicine powder which can reduce the menstruation pain is served to the user, The powder discharged from each storage barrel 200 according to the operation of the 1 or the n discharge quantity control part 110–110n is mixed and heated with a certain water discharged from the water tank 200n in the mixing and heating part 300 and then puts to the cup which droops and the user drinks the oriental medicine tea.

Namely, in accordance with the vending machine according to the present invention, if the user inserts coins, the controller 30 in FIG. 2 detects a coin inserted in step S1, and the controller decides if the user selects a certain oriental medicine tea (tea for a hangover removal, a jujube tea) in step S2, the oriental medicine tea discharged from storage barrel is provided to the user.

However, if the user don't select a certain oriental medicine tea in the step S2, the user's blood pressure (pulse) measured and user's iris photographed are supplied to the controller 30, the controller 30 checks user's health in step S4, selects related diagnosis data and controls the operation of a discharge quantity control part in step S6 in order to discharge decided quantity of oriental medicine tea from each storage barrel 200.

INDUSTRIAL APPLICABILITY

As has been explained heretofore, according to the oriental medicine tea vending machine according to the present invention, the vending machine checks user's health and serves a certain oriental medicine tea mixing various oriental medicine powder depend on the health condition of a user (disease), so that it have a good effect of improving user's health.

What is claimed is:

1. A vending machine for oriental tea comprising:
   a monitor for displaying manual of the vending machine, a user's pulse and health condition and advertising screen;
   a monetary detection part for detecting whether coins (bills) or credit card are inputted or not to operate the vending machine;
   a pulse detection part detecting the user's pulse and outputting data corresponding to the pulse;
   an iris photograph part for photographing the user's iris and outputting data corresponding to the iris;
   an oriental tea selection switch for selecting any one of a kind of oriental medicine tea;
   a data input part for inputting data corresponding to sex, age, weight of the user;
   a controller for deciding the health condition of the user based on data signals outputted from the blood pressure detection part, the iris imaging part, the data input part and the oriental medicine selection switch and simultaneously outputting control signals which select various oriental medicine materials and contents which improves the health condition of the user;
   a plurality of oriental medicine material storage barrel which store various oriental medicine materials;
   a discharge controlling part which is installed around discharge hole of each of the oriental medicine material storage barrel and controls discharge quantity of various oriental medicine tea discharged from each oriental medicine storage barrel according to control signals outputted from the controller; and
   a mix and heat part for mixing and heating a certain water and various oriental medicine tea discharged from the oriental medicine storage barrel and providing the oriental tea in a cup.

2. A vending machine for oriental tea, which comprises:
   a monetary detection part for detecting whether coins (bills) or credit card are inputted or not to operate the vending machine;
   a monitor for displaying manual of the vending machine, a user's pulse and health condition and advertising screen;
   a monetary detection part for detecting whether coins (bills) or credit card are inputted or not to operate the vending machine;
   a pulse detection part detecting the user's pulse and outputting data corresponding to the pulse;
   an iris photograph part for photographing the user's iris and outputting data corresponding to the iris;
   a data input part for selecting any one of a kind of oriental medicine tea and for inputting data corresponding to sex, age, weight of the user;
   a controller for deciding the health condition of the user based on data signals outputted from the blood pressure detection part, the iris imaging part and the data input part and simultaneously outputting control signals which select various oriental medicine materials and contents which improves the health condition of the user;
   a plurality of oriental medicine material storage barrel which store various oriental medicine powder;
   a discharge controlling part which is installed around discharge hole of each of the oriental medicine material storage barrel and controls discharge quantity of various oriental medicine tea discharged from each oriental medicine storage barrel according to control signals outputted from the controller; and
   a powder package part for packaging oriental medicine powder discharged from the oriental medicine storage barrel.

3. An oriental medicine tea vending machine, which comprises:

a pulse detection part and an iris photograph part being mounted on a body of the vending machine such as coffee and beverage vending machine for diagnosing user's health condition;

a controller for outputting control signals, based on results of the user's health diagnosis, which select various oriental medicine materials and contents which improves the health condition of the user;

a plurality of oriental medicine material storage barrel which store various oriental medicine materials; and a discharge controlling part which is installed around discharge hole of each of the oriental medicine material storage barrel and selectively discharges the oriental medicine material powder in each oriental medicine storage barrel according to control signals outputted from the controller into a powder package part or a mixing and heating part which mixes and heats a certain water and oriental medicine material powder tea discharged from the oriental medicine storage barrel and provides the oriental tea in a cup.

4. The oriental medicine tea vending machine as claimed in claim 3, wherein each oriental medicine storage barrel have different size, and the inside lower part of each of barrels is provided with means which detects the remains of high concentrated oriental medicine powder in low side of inside and supply corresponding data through the controller to a monitor which displays the remnants are notified in distance.

5. An oriental medicine tea vending machine, which comprises:

a health diagnosis means being mounted on a body of the vending machine such as coffee and beverage vending machine for diagnosing user's health condition;

a controller for deciding user's health condition based on data outputted from the health diagnosis means and for outputting data which select various oriental medicine materials and contents which improve the health condition of the user; and a discharge controlling part which is installed around discharge hole of each of the oriental medicine material storage barrel and automatically controls the discharges quantity of the oriental medicine material powder from each oriental medicine storage barrel according to control signals outputted from the controller.

* * * * *